(12) United States Patent
Gu et al.

(10) Patent No.: US 12,714,512 B2
(45) Date of Patent: Aug. 25, 2026

(54) DRIFT CORRECTION FOR MIXED REALITY IN SURGICAL ENVIRONMENTS

(71) Applicants: Arthrex, Inc., Naples, FL (US); The Johns Hopkins University, Baltimore, MD (US)

(72) Inventors: Wenhao Gu, Baltimore, MD (US); Mathias Unberath, Baltimore, MD (US); Jonathan Knopf, Naples, FL (US)

(73) Assignees: Arthrex, Inc., Naples, FL (US); The Johns Hopkins University, Bsltimore, MD (US)

( * ) Notice: Subject to any disclaimer, the term of this patent is extended or adjusted under 35 U.S.C. 154(b) by 214 days.

(21) Appl. No.: 18/630,222

(22) Filed: Apr. 9, 2024

(65) Prior Publication Data

US 2025/0312103 A1 Oct. 9, 2025

(51) Int. Cl.

| | |
|---|---|
| ***A61B 34/20*** | (2016.01) |
| ***A61B 90/00*** | (2016.01) |
| ***G06T 7/33*** | (2017.01) |
| ***G06T 7/73*** | (2017.01) |

(52) U.S. Cl.

CPC ............ *A61B 34/20* (2016.02); *A61B 90/361* (2016.02); *G06T 7/337* (2017.01); *G06T 7/73* (2017.01); *A61B 2034/2065* (2016.02); *A61B 2090/365* (2016.02); *G06T 2207/30196* (2013.01); *G06T 2207/30244* (2013.01)

(58) Field of Classification Search

None

See application file for complete search history.

(56) References Cited

U.S. PATENT DOCUMENTS

| | | | | |
|---|---|---|---|---|
| 2005/0165292 | A1 | 7/2005 | Simon et al. | |
| 2007/0225553 | A1 * | 9/2007 | Shahidi | A61B 90/36 600/103 |
| 2010/0191088 | A1 | 7/2010 | Anderson et al. | |
| 2018/0185113 | A1 * | 7/2018 | Gregerson | A61B 90/37 |
| 2018/0235715 | A1 * | 8/2018 | Amiot | A61B 34/10 |
| 2020/0233259 | A1 | 7/2020 | Yamazaki et al. | |
| 2023/0019543 | A1 * | 1/2023 | Nikou | A61B 8/4263 |
| 2023/0363832 | A1 | 11/2023 | Mosadegh et al. | |
| 2024/0299100 | A1 * | 9/2024 | Minne | A61B 90/25 |
| 2025/0302546 | A1 * | 10/2025 | Dumpe | A61B 34/20 |

FOREIGN PATENT DOCUMENTS

| | | |
|---|---|---|
| EP | 4074255 A1 | 10/2022 |

* cited by examiner

*Primary Examiner* — James A Thompson

(74) *Attorney, Agent, or Firm* — Price Heneveld LLP

(57) ABSTRACT

A method for tracking patient features in a surgical field includes capturing an image stream in a field of view demonstrating patient features of a patient anatomy. A first feature set is identified in a tracking region of the field of view of the image stream. The relative motion among a first plurality of the image features in the first feature set is monitored in the image stream over time. Moving features from the first features set are filtered to generate a second feature set. The second feature set defines tracking features. The location and orientation of the patient anatomy is then tracked based on the feature locations of the plurality of tracking features.

21 Claims, 9 Drawing Sheets

54a
54a
24
54a
56
54a
54a
54a
90
54a
92

DRIFT CORRECTION FOR MIXED REALITY IN SURGICAL ENVIRONMENTS

BACKGROUND

The present disclosure generally relates to a surgical visualization system and, more particularly, relates to various methods for motion detection and drift correction for medical or surgical applications. Traditional approaches for conducting surgical procedures commonly include the use of expensive, procedure-specific fixtures and/or experienced-based techniques to successfully complete procedures. The disclosure provides for advanced techniques that may be implemented with a surgical visualization system to improve the ease and accuracy of conducting advanced surgical techniques.

SUMMARY

Advanced visualization systems and techniques may provide for improved accuracy and patient outcomes for a variety of surgical procedures. However, surgical procedures are conducted in complex environments that include a wide variety of objects and corresponding moving features that may complicate vision-based processing necessary to enable many visualization systems. In various implementations, the disclosure may provide for methods and systems for tracking patient features in a surgical field with a camera. By accurately tracking the patient features in a field of view of the camera, the disclosure may provide for accurate pose detection and drift correction, allowing surgical guidance and/or information to be accurately presented in alignment with the patient anatomy on a display screen. As provided in various detailed examples in the following description, the disclosure may provide for improved pose tracking and drift correction for a camera of the visualization system to achieve the improved operation.

In a specific example, the camera may capture an image stream including a plurality of frames in a field of view demonstrating image features representative of a patient anatomy. The image features may be identified in a tracking region that may be defined relative to a point of interest or anatomic reference point associated with a surgical procedure. Within the tracking region, a first feature set may be identified and monitored to identify relative motion among the image features in the image stream over time. A plurality of tracking features may then be identified from the first feature set by filtering one or more moving features from the first plurality of image features to generate a second feature set. The location and orientation of the patient anatomy, as well as the pose or relative position and orientation of the camera relative to the anatomy, may then be tracked based on feature locations of the tracking features that may change or be updated in the image stream over time.

In operation, the image features corresponding to the tracking features of the patient anatomy may be filtered over time to improve accuracy and limit tracking errors. The image features may be filtered based on motion relative to the patient anatomy. In some cases, the image features may be limited based on the dimensions of a tracking region that may be defined by predetermined proportions relative to a point of interest or anatomic feature of the patient associated with the surgical procedure. In other implementations, the tracking features may be limited based on an identity or type of object associated with the image features identified in the image stream. For example, one or more disruptive objects (e.g., a retractor, drape, etc.) may be identified based on the image features in the image stream. Once identified, the features associated with the disruptive object may be filtered or removed from those considered to define the tracking features for the patient anatomy. In this way, abrupt changes to the tracking features may be avoided over time to improve the tracking of the patient anatomy and the corresponding pose tracking of the camera system.

These and other features, objects and advantages of the present disclosure will become apparent upon reading the following description thereof together with reference to the accompanying drawings.

DETAILED DESCRIPTION

In the following description, reference is made to the accompanying drawings, which show specific implementations that may be practiced. Wherever possible, the same reference numbers will be used throughout the drawings to refer to the same or like parts. It is to be understood that other implementations may be utilized and structural and functional changes may be made without departing from the scope of this disclosure.

Figure 1:
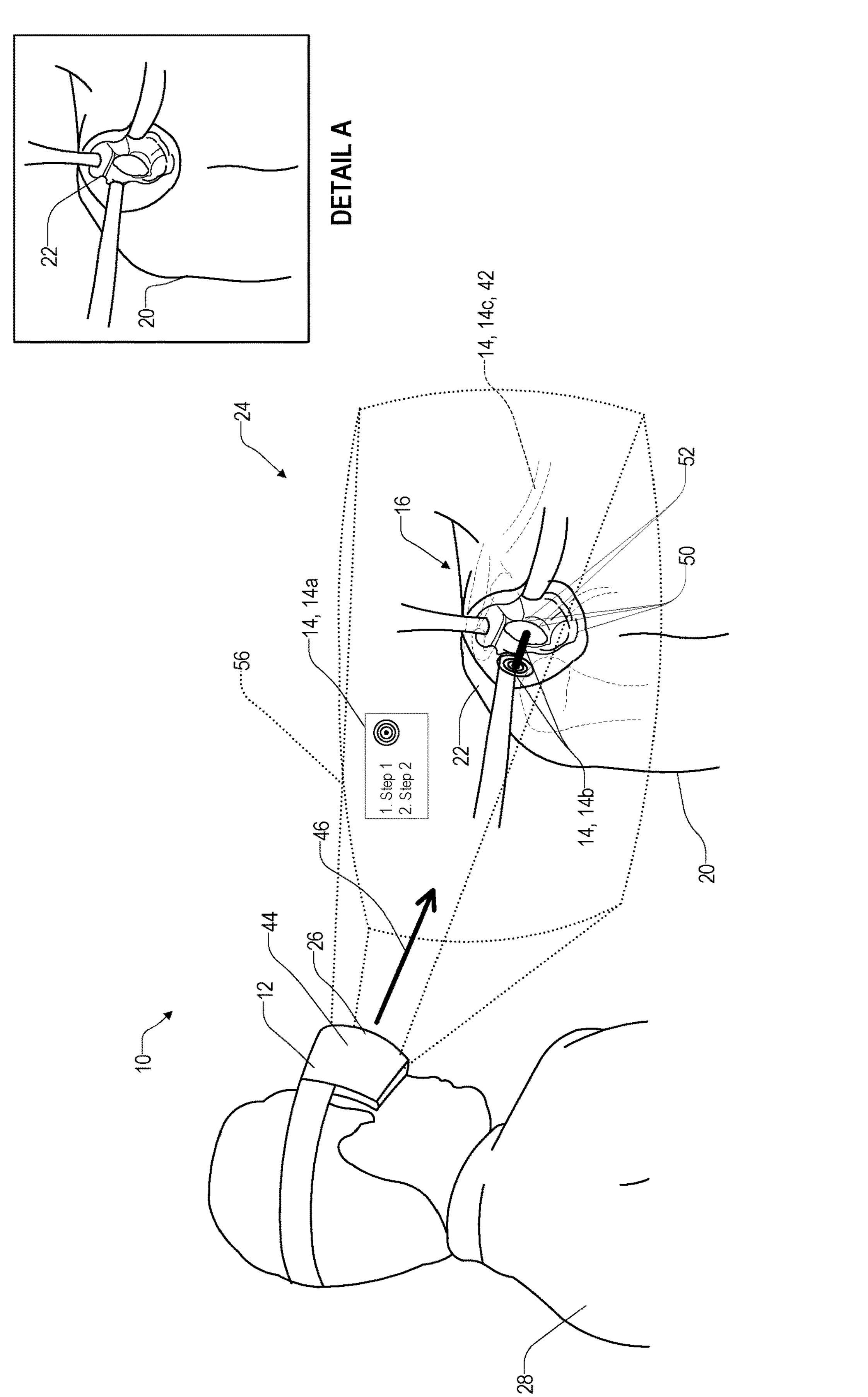
FIG. 1 is an environmental view demonstrating a surgical visualization system implemented in a surgical procedure.

Referring to FIG. 1, the operation of a surgical visualization system 10 is shown demonstrating a head-mounted display device 12 presenting one or more enhanced visuals or display information 14 superimposed over a region of interest or operating region 16 of a patient 20. As shown, the display information 14 may correspond to one or more instructions **14*a*, surgical guides 14*b*, patient data 14*c* (e.g., imaging, bone models, scan data, etc.), and/or additional information relevant to a surgical procedure (e.g., time elapsed, patient vitals, etc.) that may be presented in coordination with one or more features of an anatomy 22 of the patient 20. For example, the display information 14 may be presented on a display screen 26 of the head-mounted display 12 in a surgical field 24 adjacent to the operating region 16. In the example shown, the display screen 26 is a transparent display through which the enhanced display information 14 is presented in alignment with the corresponding anatomy 22 of the patient 20. However, the display screen 26 may similarly be implemented as an opaque video screen. As shown by comparison to Detail A, the features of the display information 14 may be superimposed over the anatomy 22 of the patient 20 to improve the ease and accuracy of various procedures by providing visual references, such as the view of the alignment guide and corresponding instructions 14***a* to a medical professional 28. In this way, the visualization system 10 may provide for enhanced accuracy in various surgical procedures and resulting improved patient outcomes.

Figure 2:
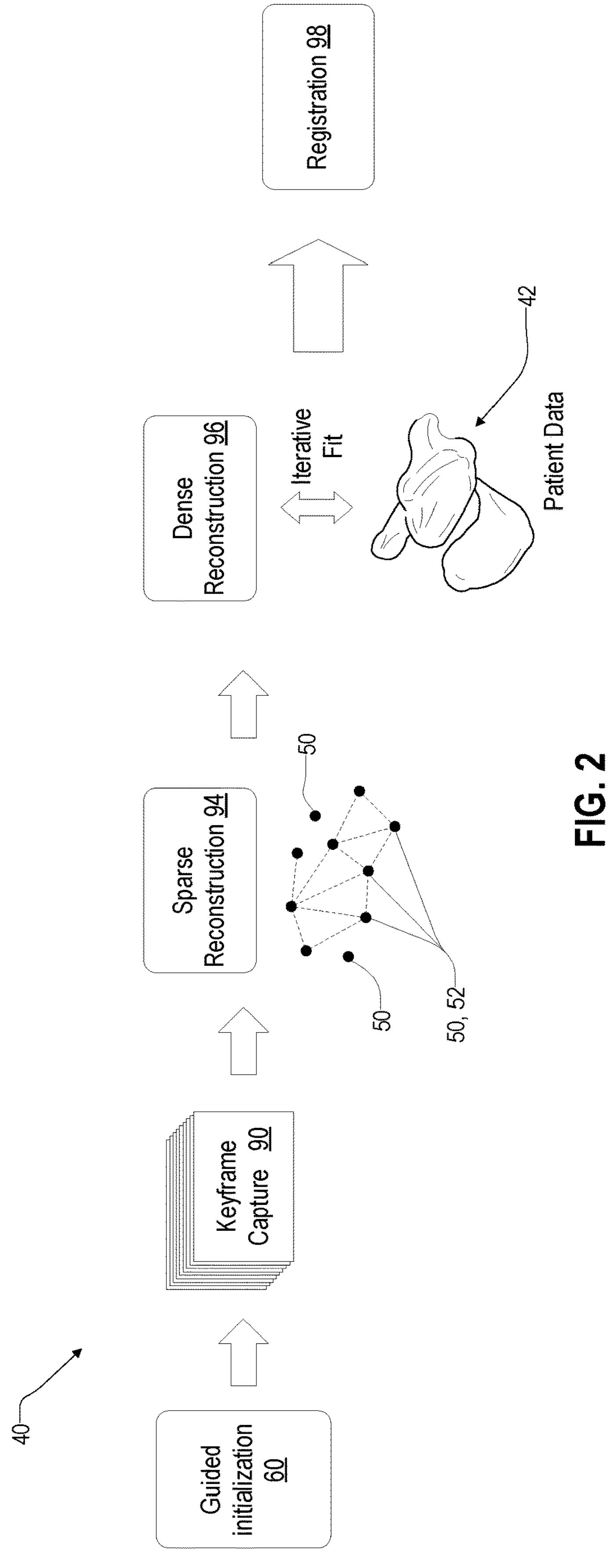
FIG. 2 is a process diagram demonstrating a registration procedure for a visualization system.

As generally demonstrated in FIG. 2, the visualization system 10 may provide for the alignment of the display information 14 relative to the anatomy 22 via a registration process 40. As discussed in further detail in reference to FIGS. 2-5, the registration process 40 may align the patient data 42 or a patient model to the anatomy 22 of the patient 20. Further, the registration process 40 may provide for the pose detection of a camera apparatus 44 of the head-mounted display 12. With the pose (e.g., position and orientation) of the camera apparatus 44, the system 10 may present the enhanced display information 14 or guidance positioned on the display screen 26 in alignment with the corresponding anatomy 22 relative to a visual perspective 46 of the medical professional or surgeon 28. As best demonstrated in FIG. 5, the accurate alignment of the display information 14 to the anatomy 22 of the patient 20 based on the image data captured by the camera apparatus 44 may depend on the identification of image features 50 that reliably correlate to the position of the anatomy 22. These image features 50 representative of the position and orientation of the anatomy 22 are referred to as tracking features 52 and may be identified by the system 10 via methods described later in reference to FIGS. 6-8.

Figure 5:
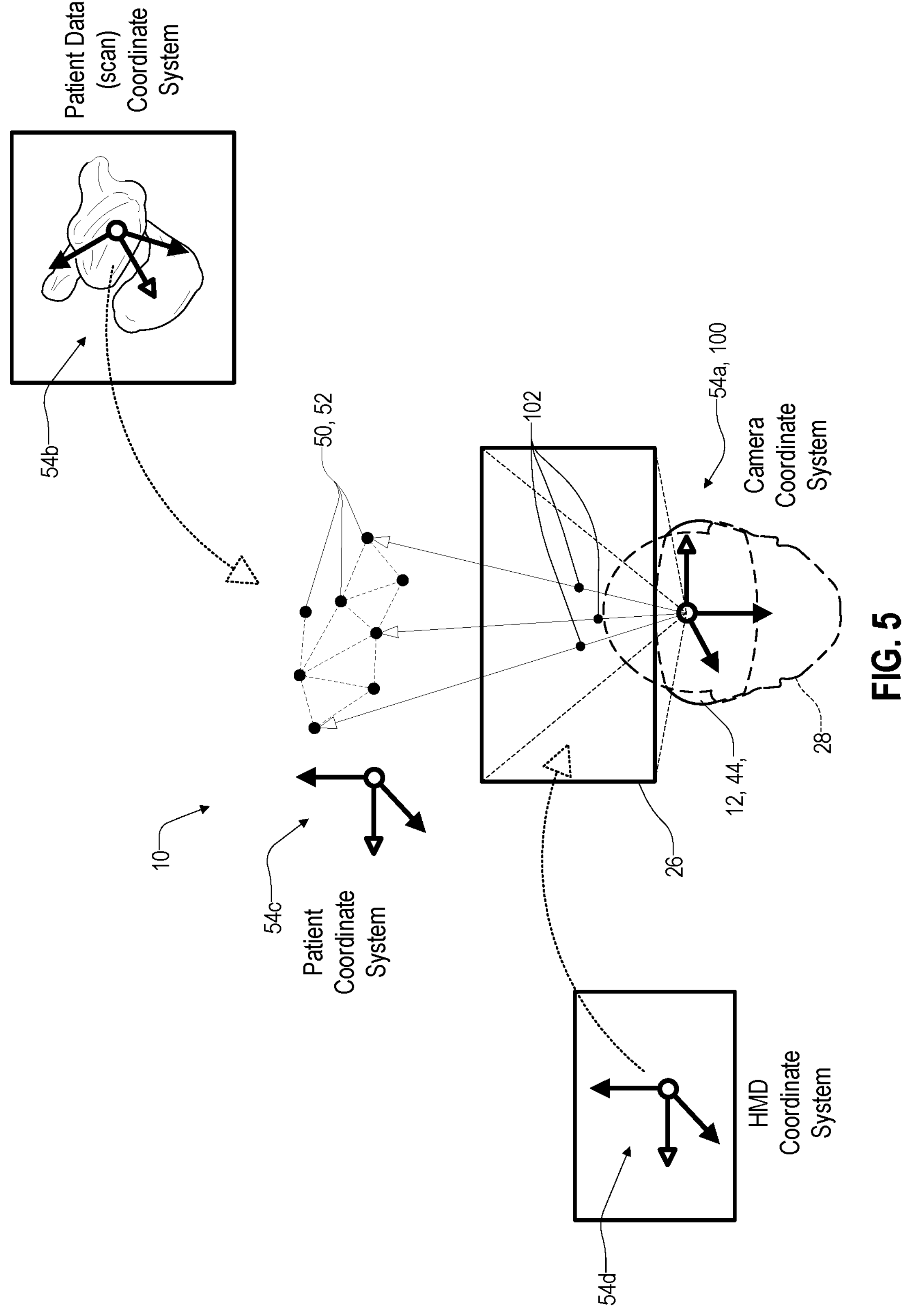
FIG. 5 is a process diagram demonstrating a best fit registration of patient data to a patient coordination system and pose detection of a camera coordination system to the patient coordination system.

In operation, the presentation of the display information 14 may require the alignment and relative position tracking (e.g. pose detection) of a plurality of coordinate systems 54 within a common or global coordinate system. As shown in FIG. 5, the coordinate systems 54 may include a camera coordinate system 54*a*, a model coordinate system 54*b* (e.g., patient data), a patient coordinate system 54*c*, and a display coordinate system 54*d*. The accurate positioning of the display information 14 on the display screen 26 based on the image data captured in the field of view 56 may present various challenges. In various implementations, the disclosure provides for improved positioning of the coordinate systems 54 by filtering and selecting the tracking features 52 from the image features 50 throughout operation. The disclosure provides for various methods and techniques that may prevent drift of the display information 14 relative to the anatomy 22 of the patient 20 to improve the operation of the visualization system 10.

Figure 3:
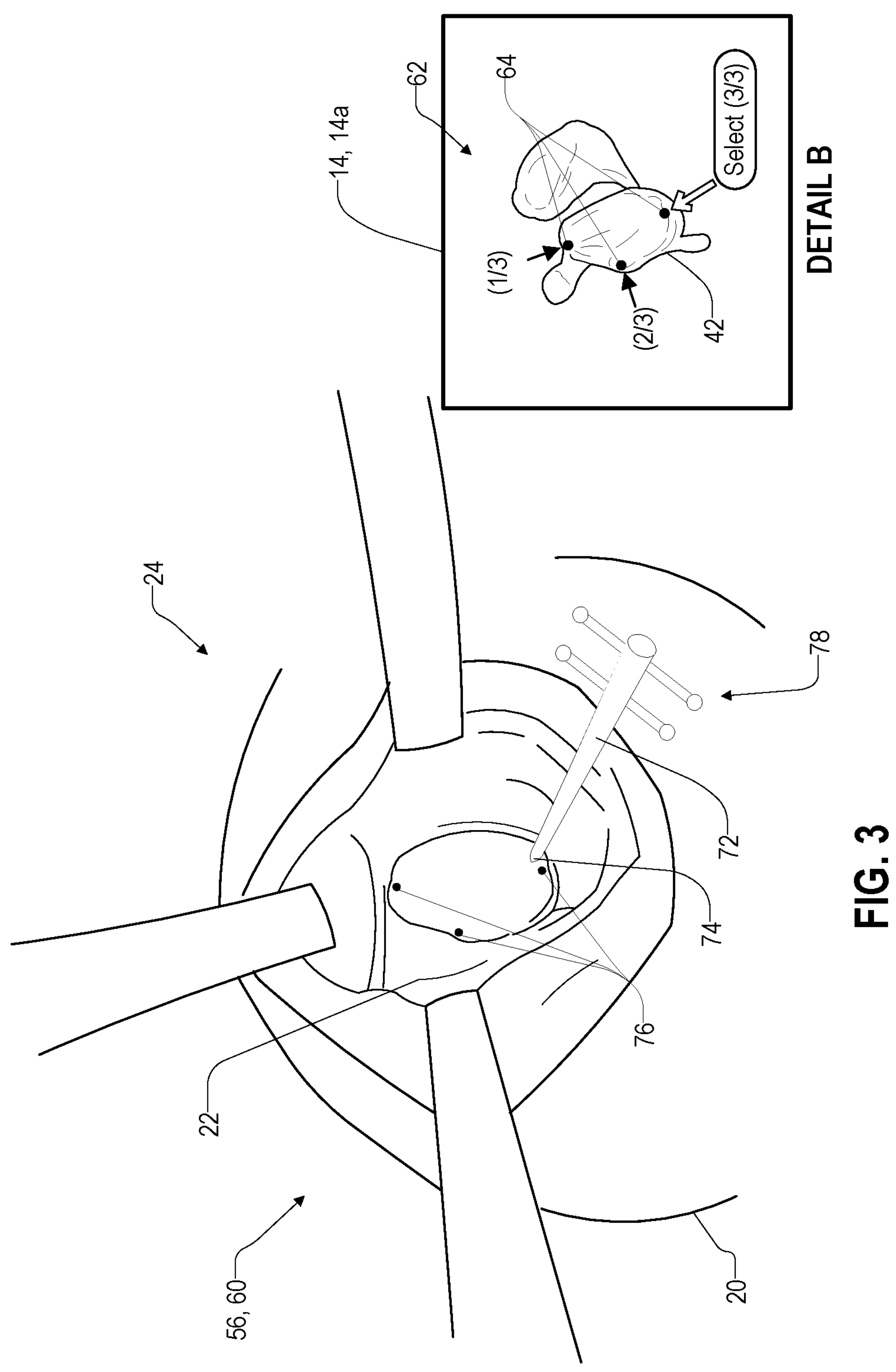
FIG. 3 is an exemplary diagram demonstrating an initialization process for registering patient data to anatomic landmarks in an interoperative image.

Referring to FIGS. 2-5, the registration process 40 is described in further detail. As shown in FIG. 3, a guided initialization process 60 may first be implemented to provide a rough alignment of the patient data 42 to the corresponding anatomy 22 captured in the field of view 56. In operation, the guided initialization process 60 may provide interactive instructions 62, as shown in Detail B, which may be presented as a portion of the display information 14 on the display screen 26. The interactive instructions 62 demonstrated in FIG. 3 illustrate a plurality of landmarks 64 superimposed over the patient data 42 or patient model identifying characteristics of the anatomy 22 of the patient 20 that may be aligned by one or more controllers or processing servers 70 of the visualization system 10 to estimate the alignment between the patient data 42 of the patient 20 to the anatomy 22. The selection of the landmarks 64 within the surgical field 24 and on the anatomy 22 of the patient 20 may be identified by a stylus or pointer 72 that may be guided by the surgeon or operator 28 to align a calibrated distal tip 74 with each of the landmarks 64 in a sequence identified on the interactive instructions 62. In this way, the operator or medical professional 28 may identify each of the landmarks 64 on the anatomy 22 within the surgical field 24 to provide a rough alignment of the patient data 42 to the exposed anatomy 22 demonstrated in the image data captured by the camera apparatus 44.

In addition to the interactive instructions 62 demonstrated in Detail B, graphic representations 76 of the landmarks 64 may be superimposed over the view of the anatomy 22 provided through the display screen 26. In this way, tracked operation of the stylus or pointer 72 via the camera apparatus 44 may be visually demonstrated and confirmed on the display screen 26 of the head-mounted display device 12. In operation, the manual inputs or movements associated with the stylus 72 may be tracked by the camera apparatus 44 by identifying a location of the calibrated distal tip 74 relative to a fiducial marker 78. In this way, rough estimates of the locations of the landmarks 64 may be manually identified to complete the guided initialization 60.

As described herein, the landmarks 64 may correspond to predefined features identified in the patient data 42 during a planning phase for a surgical procedure. For example, a planning technician may identify one or more readily discernable features in the patient data 42 that may be identified intraoperatively on the anatomy 22 of the patient 20. Accordingly, the landmarks 64 may correspond to visual features that may be identified on the anatomy 22 via the interactive instructions 62. By identifying the landmarks 64, the operator 28 may provide a rough alignment of the patient data 42 (e.g., 3D model data) captured preoperatively to the anatomy 22 of the patient 20 captured intraoperatively in the image data by the camera apparatus 44.

Figure 4:
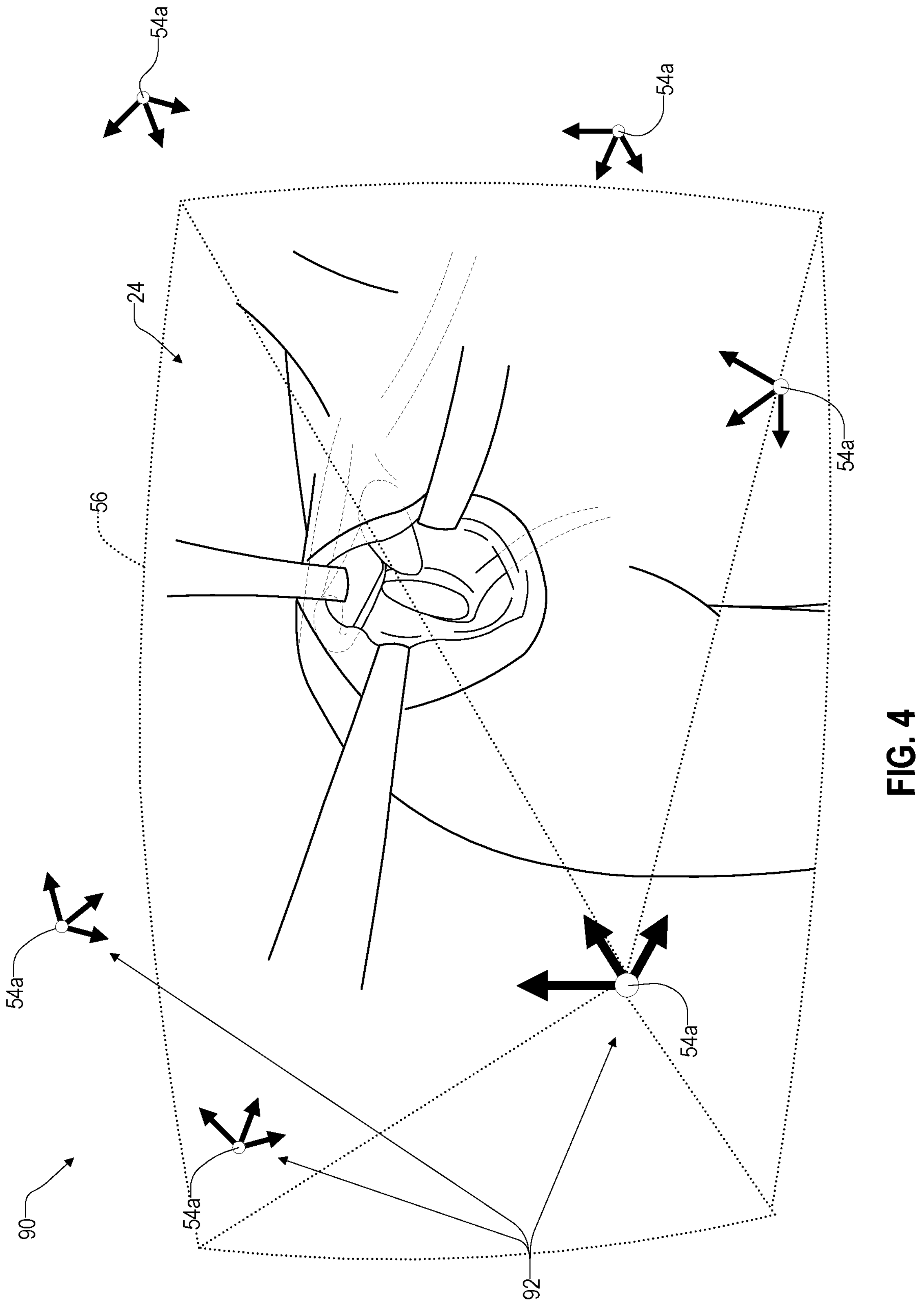
FIG. 4 is a representative diagram demonstrating a key frame image capture procedure for registration of the patient data.

Referring now to FIGS. 2 and 4, the registration process 40 may continue by proceeding to a key frame capture process 90. As shown in FIG. 4, the key frame capture process 90 may involve orienting a camera coordinate system 54*a* of the camera apparatus 44 at a plurality of positions 92 and corresponding orientations with the field of view 56 aligned with the surgical field 24. The image data captured at the plurality of positions 92 may correspond to key frame images that may be applied by the controllers or processing servers 70 of the system 10 to generate a reconstruction of the anatomy 22. For example, the image data from the key frame images may be implemented to run a structure for motion (SFM) processing method to generate a sparce reconstruction 94 and may further be applied via a multi-view stereo (MVS) processing method to generate a dense reconstruction 96 of the anatomy 22 demonstrated in the surgical field 24. The dense reconstruction 96 of the anatomy 22 may then be used to register the scan data or patient data 42 to the anatomy 22 of the patient 20 captured in the key frame images from the plurality of positions 92 in a registration step 98. Further, the registration step 98 may determine the pose of the camera apparatus 44 or the camera coordinate system 54*a* relative to the anatomy 22 of the patient 20 as determined from the dense reconstruction 96.

As discussed herein, the scan data or patient data 42 may correspond to three-dimensional (3D) data preoperatively captured demonstrating the anatomy 22 or anatomy of interest of the patient 20. Accordingly, the patient data 42 may be captured preoperatively during the planning stages of a surgical procedure. The patient data may later be accessed by the visualization system 10 intraoperatively to assist in an alignment between the model coordinate system 54*b* of the patient data 42 to a patient coordinate system 54*c* of the anatomy 22 of the patient 20. The resulting alignment of the model coordinate system 54*b* to the patient coordinate system 54*c*, as best illustrated in FIG. 5, may be achieved via an iterative alignment process wherein the 3D features of the dense reconstruction of the anatomy 22 are aligned with corresponding features of the model generated from the patient data 42. In this way, the model coordinate system 54*b* may be accurately aligned with the patient coordinate system 54*c* for the registration 98.

Referring now to FIG. 5, the alignment of the coordinate system 54 is demonstrated and described in further detail. As previously discussed, the dense reconstruction procedure 96 may align the model coordinate system 54*b* with the patient coordinate system 54*c*. With the patient data 42 registered to the patient coordinate system 54*c*, a camera pose 100 of the camera apparatus 44 and the corresponding camera coordinate system 54*a* may be determined via a perspective-in-point (PnP) process. In operation, the PnP process may estimate the pose 100 based on the alignment of a set of N, 3D points of known features (e.g., the tracking features 52) in the patient data 42 to projections 102 (e.g., two-dimensional (2D) projections) of the tracking features 52 presented in the image data captured by the camera 44. For example, the pose 100 may be determined via simplified PnP with N=3 (P3P), Efficient PnP, Sequential Quadratic PnP, or various pose-from-perspective alignment procedures. With the camera coordinate system 54*a* of the camera apparatus 44 aligned and positioned with the patient coordinate system 54*c*, the controllers or processing servers 70 of the visualization system 10 may generate the one or more surgical guides 14*b* or corresponding graphics or images for presentation on a display coordinate system 54*d* of the display screen 26. In this configuration, the surgical guides 14*b* or other relevant information may be presented on the display screen 26 superimposed over or in alignment with the accurate positions associated with the patient data 42 to assist in various surgical procedures. Further detailed description of the controllers or processing servers 70 of the visualization system 10 are described later in reference to FIG. 9.

Figure 6:
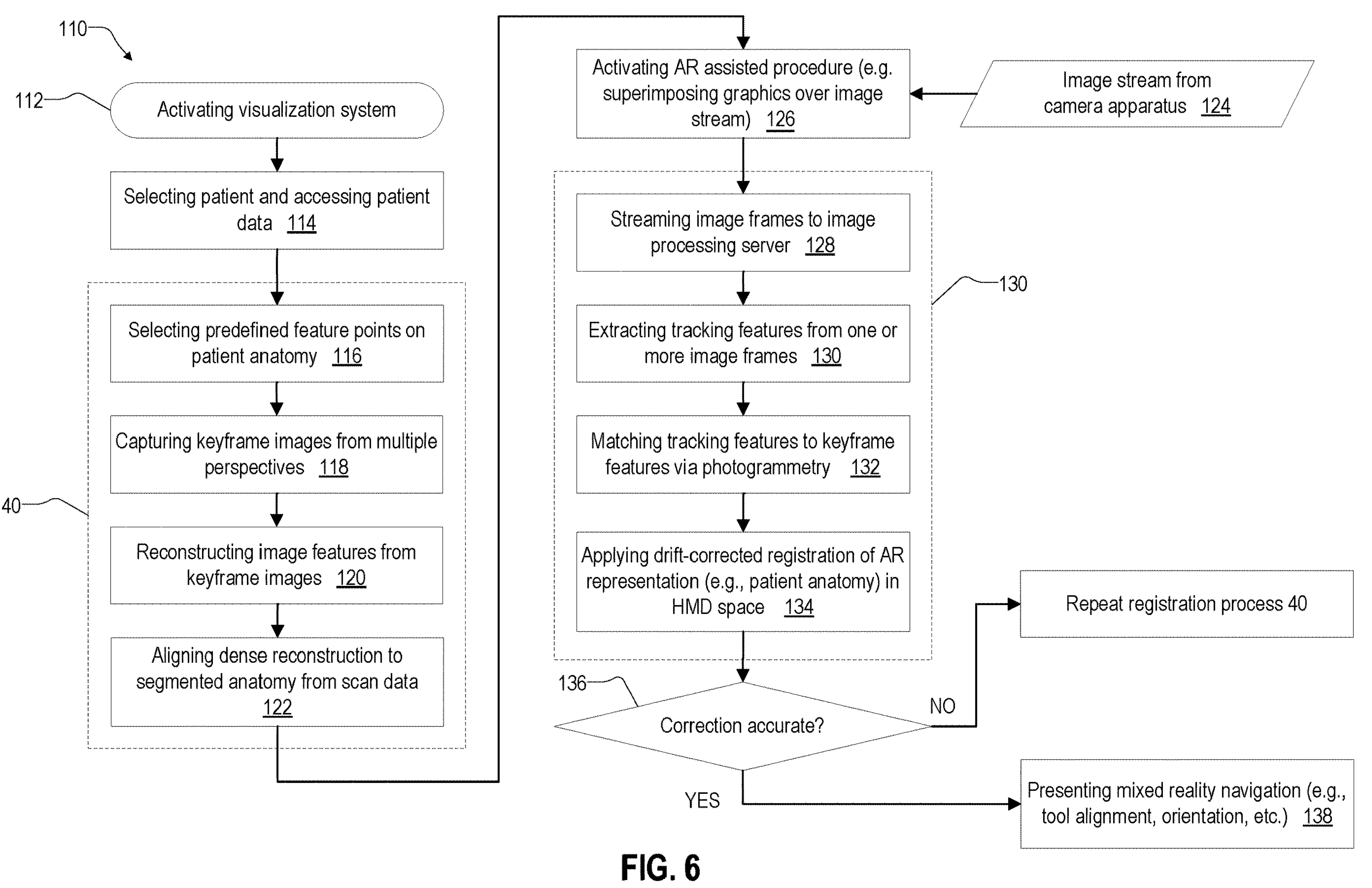
FIG. 6 is a flowchart demonstrating a method for registration and drift correction for a surgical visualization system.

Referring now to FIG. 6, a flowchart is shown demonstrating a method 110 for applying the registration process 40. In operation, the method 110 may be initiated in response to an activation of the visualization system 10 (112). Once activated, the method 110 may continue by selecting a patient and accessing the associated patient data 42, which may be stored on one or more planning or patient servers or databases (114). With patient data 42, the visualization system 10 may be controlled through the steps of the registration process 40 as previously described in reference to FIGS. 2-5. As shown in FIG. 6, the registration process 40 may include selecting the predefined features points or landmarks 64 (e.g., guided initialization 60) on the anatomy 22 in step 116 followed by capturing the key frame images (e.g., key frame capture process 90) from the plurality of positions 92 or perspectives in step 118. The sparce and dense reconstruction steps 94, 96 may be processed in step 120 and the patient data 42 may be aligned to the dense reconstruction of the segmented anatomy 22 in step 122.

Following the registration process 40, the visualization system 10 may be activated to provide a simulated overlay or augmented reality including graphics and/or images (e.g., the patient data 42) displayed on the display screen 26 aligned with the anatomy 22 identified in an image stream 124 captured by the camera 44 (126). As described herein, augmented reality may relate to the superposition of simulated graphics, images, or various visual features that may be superimposed on the display screen 26 of the head-mounted display device 12 as virtual representations or holograms over the natural environment of the operating region 16 in the surgical field 24. Augmented reality may similarly be referred to as mixed reality, extended reality, holographic simulation, virtual reality, or similar procedures. The visualization system 10 may ensure that the surgical guides 14*b* or various augmented or simulated reality instructions 14*a* are accurately superimposed on the display screen 26 over the local environment visible within the field of view 56 of the camera apparatus 44 by applying a drift correction process 130.

In operation, the drift correction process 130 may be initiated to improve the augmented reality assisted operation of the visualization system 10 as introduced in step 126. The drift correction process 130 may operate by processing one or more of the image frames received in the image stream 124 via the image processing server 70 (128). Throughout operation of the head-mounted display device 12, the image stream 124 may be processed to extract various tracking features 52 identified among a number of image features 50 (130). The tracking features 52 may be matched to key frame features identified from the key frame images (e.g., from keyframe capture process 90) via a photogrammetry process (132). By matching the tracking features 52 to the key frame features associated with the original registration 98, offsets between the tracking features 52 and the key frame features may be applied as rotational and/or translational drift correction offsets for the surgical guides 14*b* or display information 14 presented on the display screen 26 (134). In this way, the drift correction process 130 may ensure that the simulated graphics or display information 14 may be accurately superimposed and presented over the features of the anatomy 22 of the patient 20 and/or various environmental features present in the operating region 16 as detected within the field of view 56 of the camera apparatus 44.

In some implementations, the drift correction process 130 may provide for a manual assessment of the accuracy of the registration of the information or surgical guides 14*b* to the anatomy 22 or features in the field of view 56 (136). For example, if a user 28 indicates that the drift correction process 130 is accurately applied to overlay the display information 14 on the display screen 26, the method 110 may continue to present the virtual environment or display information 14 on the display screen 26 (138). If the drift correction process 130 is identified as not providing for accurate positioning of the simulated information 14 or surgical guides 14*b* on the display screen 26 in step 136 (e.g., misaligned), the method 110 may selectively reactivate the registration process 40 to improve the ongoing drift correction process 130.

Figure 7:
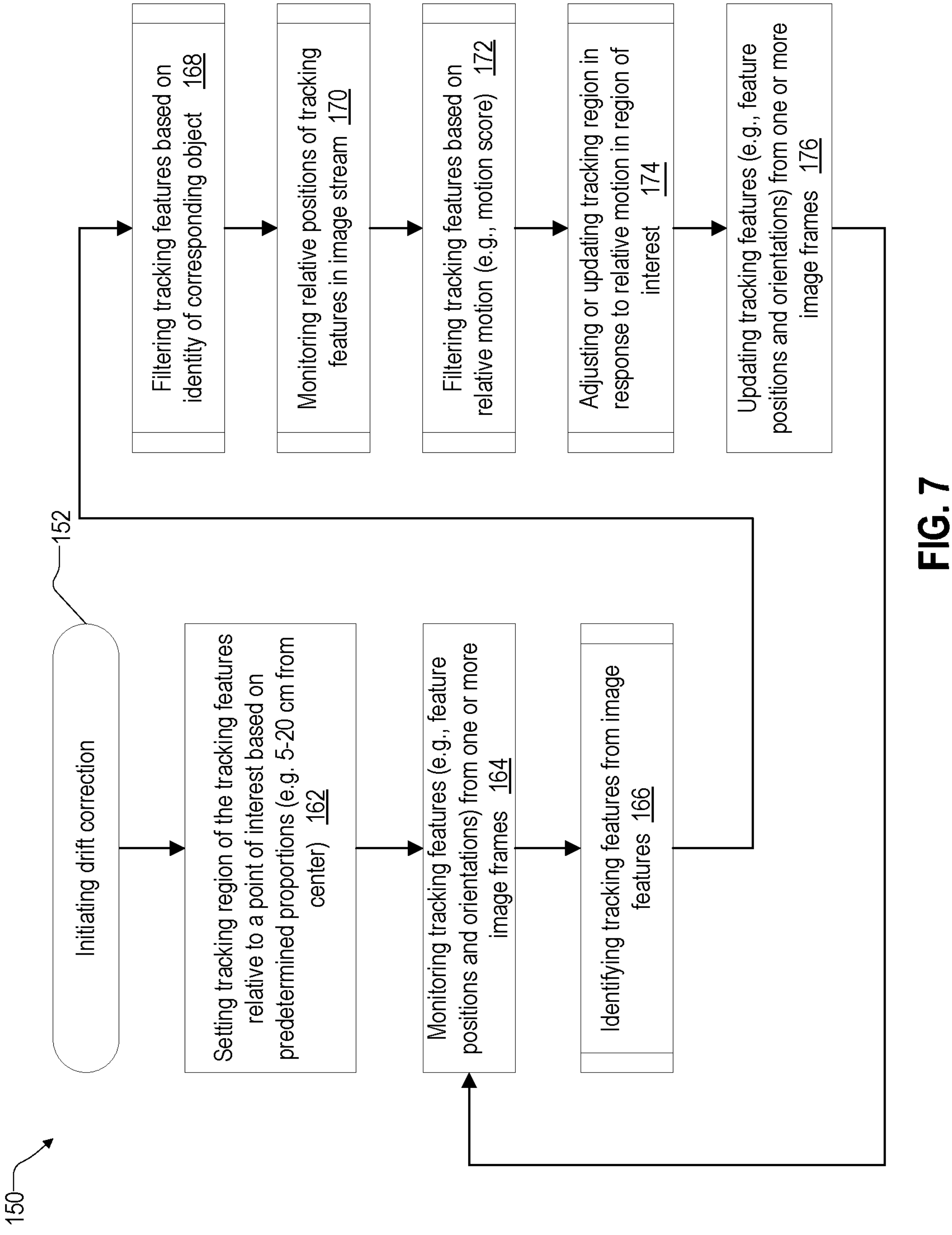
FIG. 7 is a flowchart demonstrating a detailed method for drift correction demonstrating one or more filtering steps for image features identified in an image feed.
Figure 8:
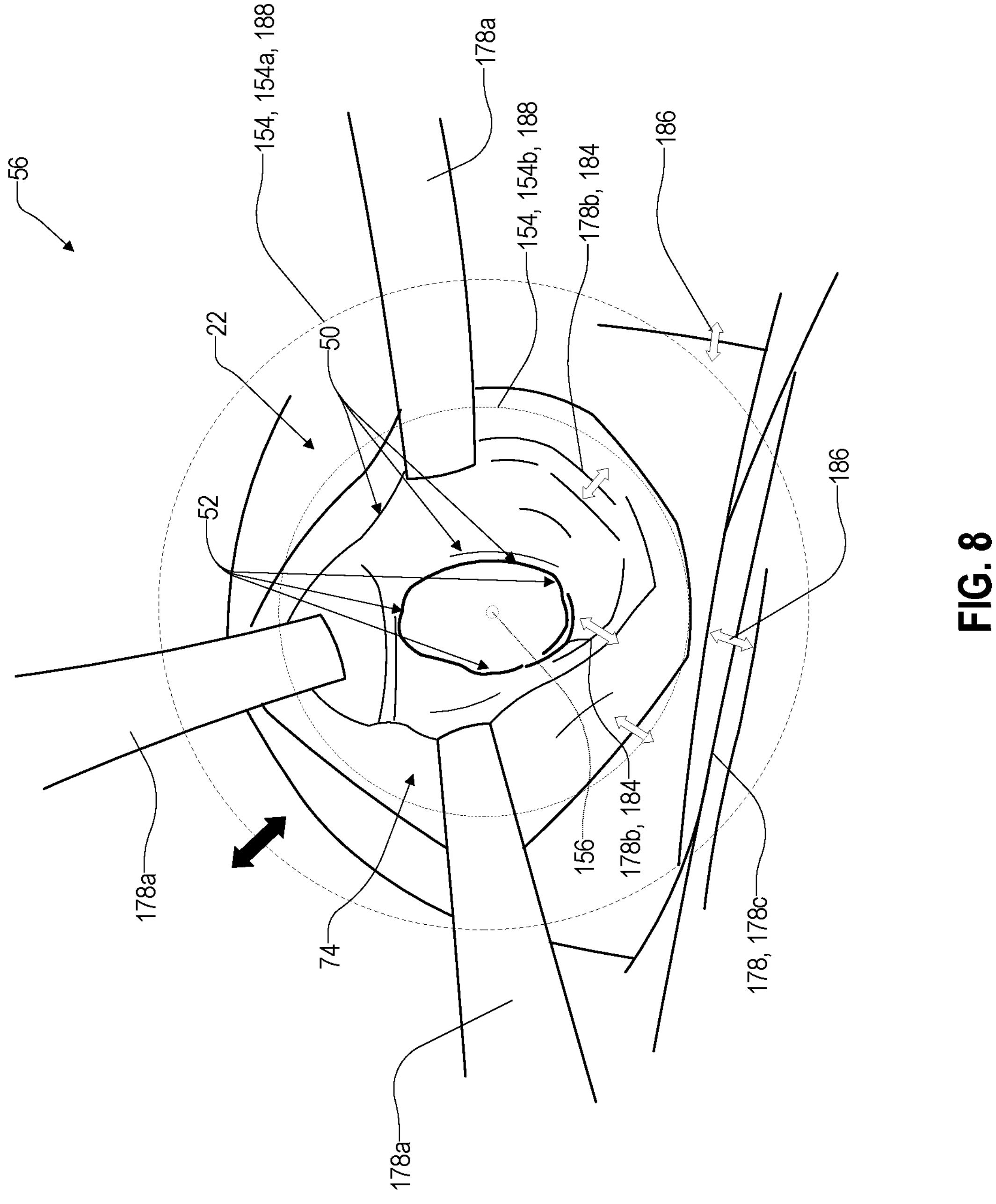
FIG. 8 is a simulated view of a surgical field within a field of view of a camera apparatus of a head-mounted display device.

In addition to the general steps of the drift correction process 130 as introduced in FIG. 6, FIGS. 7 and 8 may provide for additional operations that may improve the drift correction process 130 throughout the operation of the visualization system 10. In some implementations, the drift correction process 130 may include one or more feature tracking or region tracking routines 150 that may be applied alone or in combination to improve the operation of the drift correction process 130. Following initialization of the drift correction process 130 in step 152, a tracking region 154 may be defined relative to a point of interest 156 within which various image features 50 may be identified and processed to identify tracking features 52 for the drift correction process 130 (162). For example, as demonstrated in FIG. 8, the image data presented in the field of view 56 captured by the camera apparatus 44 may include a variety of image features 50, which may correspond to various lines, shapes, variations in color and/or contrast, or other detectable features presented in the image stream 124. The point of interest 156 may correspond to a central region within the surgical field 24, which may correspond to or be offset from one or more of the image features 50. Accordingly, the tracking region 154 may initially be defined based on predetermined proportions or dimensions that may be associated with the specific procedure and/or the physiology of the patient 20.

The point of interest 156 may be defined in a preoperative planning step, wherein the patient data 42 associated with the anatomy 22 may be reviewed and annotated to identify the point of interest 156. In this way, the point of interest 156 may be identified based on the particular needs of the patient 20 in relation to the anatomy 22 that may be central to the surgical procedure being performed. With the point of interest 156 identified, the tracking region 154 may be set or defined based on one or more predetermined dimensions extending from or measured relative to the point of interest 156 in step 162. Throughout the drift correction process 130, the image features 50 within the tracking region 154 may be monitored to identify changes in the camera pose 100 and corresponding adjustments to the field of view 56 of the camera apparatus 44 and the repositioning of the display screen 26 relative to the operating region 16 (158). As further described in the detailed steps that follow, the image features 50 may be selected by the controller(s) or processing server(s) 70 of the visualization system 10 to ensure that the tracking features 52 utilized for the drift correction process 130 are accurate indicators of the position and/or orientation of the corresponding anatomy 22 of the patient 20.

As outlined in steps 166-176, the visualization system 10 may adjust the tracking region 154 as well as the image features 50 utilized as tracking features 52 to ensure the drift correction process 130 accurately updates the pose 100 of the camera coordinate system 54*a* and the model and patient coordinate systems 54*b*, 54*c*. For example, in step 166, the tracking features 52 may be identified among a plurality of image features 50 from the registration process 40. As previously discussed in step 132, the tracking features 52 may be identified as image features 50 that correspond to key frame features identified in the dense reconstruction process 96. However, throughout operation of the drift correction process 130, one or more of the tracking features 52 may be filtered or removed from the list of tracking features 52 used to track the relative motion of the head-mounted display device 12 to the patient 20 and vice versa. In this way, the system 10 may ensure that the tracking features 52 and the tracking region 154 are consistently updated to improve the accuracy of tracking the positions of the patient 20 and the camera apparatus 44.

In some cases, the tracking features 52 may be filtered based on an identity of one or more objects detected within the field of view 56 (168). For example, the one or more controllers or processing servers 70 of the visualization system 10 may determine the identity of one or more of the objects, for example, a retractor 178*a*, soft tissue 178*b*, and/or a drape 178*c* within the field of view 56. Such features 178*a*, 178*b*, 178*c* or similar features may correspond to disruptive features 178 that may unexpectedly change in position after extended periods of consistent positioning relative to the anatomy 22 of the patient 20. Accordingly, the drift correction process 130 may filter such objects from the tracking features 52 to prevent unexpected changes in the position of the tracking features 52 relative to the anatomy 22 of the patient 20. Filtering the disruptive features 178 from the candidates of the image features 50 considered for the tracking features 52 may prevent errors in the alignment between the surgical guides 14*b* or simulated display information 14 presented on the display screen 26 relative to the anatomy 22.

In addition to filtering the disruptive features 178 from the tracking features 52, in steps 170-172, the method 150 may filter or remove one or more of the tracking features 52 from consideration for the drift correction process 130. In operation, the system 10 may remove the tracking features from consideration based on changes in relative positions among the features within the image stream 124. As demonstrated in FIG. 8, the controllers or processing servers 70 of the visualization system 10 may identify one or more of the image features 50 or tracking features 52 as moving features 184. As shown, arrows 186 may illustrate the relative motion of the moving features 184 relative to the tracking features 52 as detected over time within images or groups of images in the image stream 124. In response to identifying the moving features 184, the method 150 may filter the moving features 184 from the tracking features 52 in step 174. For example, the movement of the moving features 184 may be identified as having one or more relative motion scores or change vectors that fail to correlate to the majority of the tracking features 52 over time within the image stream 124. Accordingly, such moving features 184 may be filtered or removed from the tracking features 52 to improve the operation of the drift correction process 130.

In addition to adjusting or filtering the tracking features 52, the method 150 may further provide for the adjustment or updating of the tracking region in step 174. For example, as shown in FIG. 8, the tracking region 154 may be adjusted in proportions or dimensions from the first tracking region 154*a* to the second tracking region 154*b*. In the example shown, the second tracking region 154*b* may correspond to a smaller region within the field of view 56 that may be resized or adjusted in proportion or position relative to the point of interest 156. In operation, the proportions or perimeter 188 of the tracking region may be updated in response to the moving features 184 and/or the identities of the disrupted features 178. In this way, the method 150 may adjust the proportions of the tracking region 154, such that the perimeter 188 of the tracking region 154 is adjusted to exclude various disruptive features 178 and/or moving features 184 from the tracking region 154. In other cases, the proportions of the tracking region 154 may alternatively be increased to include additional tracking features 52. In this way, the method 150 may update the tracking features 52 based on the activity of one or more of the image features 50 identified in the image stream 124 (176). The operation of the drift correction process 130 may continue throughout the operation of the visualization system 10 to provide ongoing alignment of the surgical guides 14*b* or similar augmented information to the head-mounted display device 12.

Figure 9:
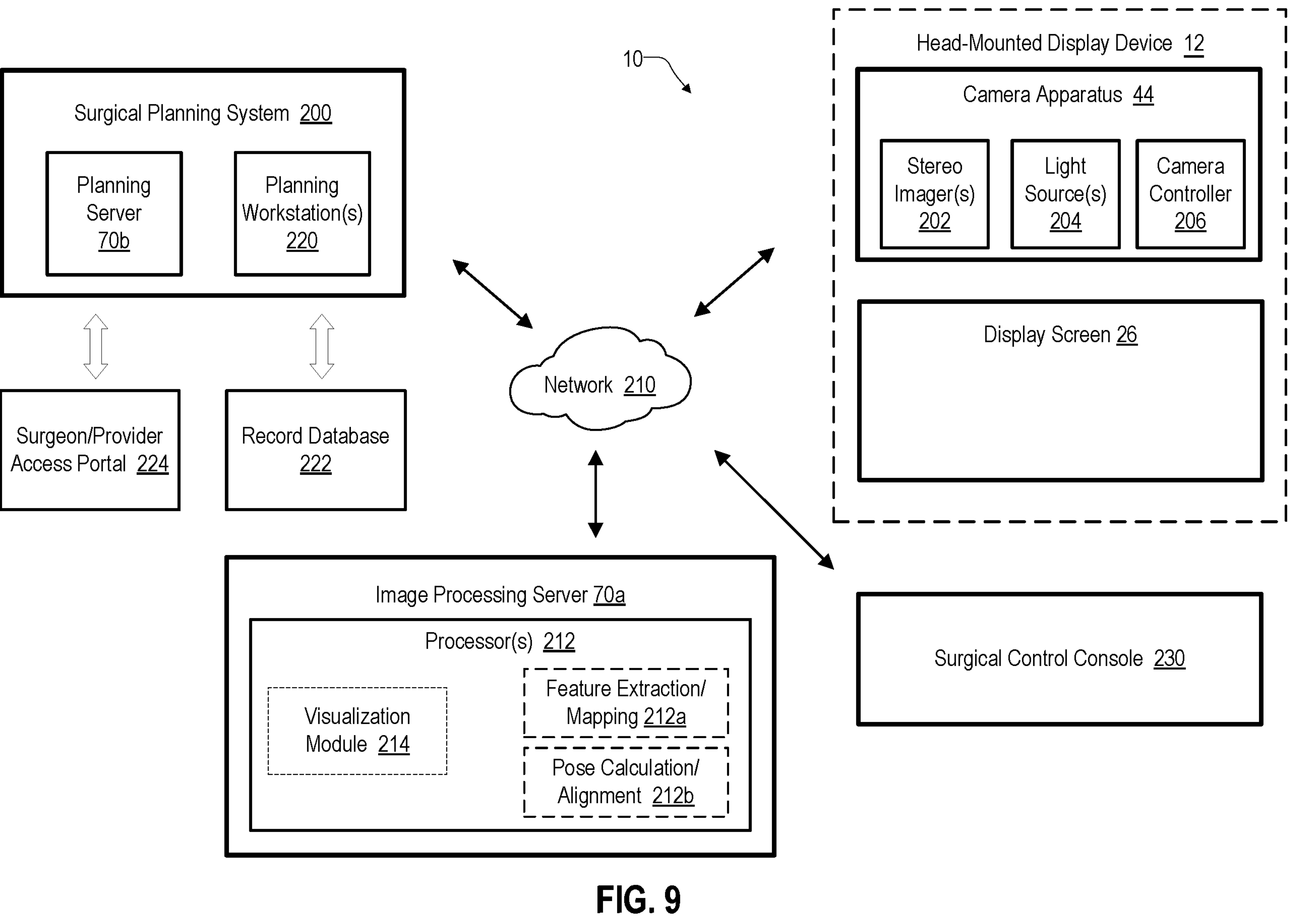
FIG. 9 is a simplified block diagram demonstrating the visualization system operating in coordination with a surgical planning system.

Referring now to FIG. 9, a block diagram of the visualization system 10 is shown including the controllers or processing servers 70 and a surgical planning system 200. As previously discussed, the visualization system 10 may include one or more controllers or processing servers 70, demonstrated in the example of FIG. 9 as an image processing server 70*a* and a planning system 200. In the example shown, the head-mounted display device 12 includes both the camera apparatus 44 and the display device 12. However, the methods disclosed need not require these devices provided in combination. More generally, it should be understood that the specific processing or computational devices, programmable controllers, memory or storage utilities, and related electronic hardware of the system 10 may vary widely depending on the specific application.

As shown in FIG. 9, the visualization system 10 may comprise the head-mounted display device 12 incorporating the camera apparatus 44 and the display screen 26. Additionally, the camera apparatus 44 may include one or more sensors (e.g., image sensors, optical sensors, depth sensors, motion sensors, etc.), which may be implemented to capture the image stream 124 and corresponding depth or surface profile information within the field of view 56. In some implementations, the sensors may include one or more cameras or imagers, which may correspond to a stereoscopic imager 202. The one or more imagers may be configured to capture light in one or more ranges of wavelengths or spectrums including, but not limited to, a visible light spectrum ranging from approximately 380 nm to 700 nm and a near infrared (NIR) light spectrum ranging from approximately 760 nm to 2500 nm. The camera apparatus 44 may further incorporate one or more light sources 204, which may be integrally incorporated in the head-mounted device 12 or separately provided as lighting modules. The one or more light sources 204 may be configured to emit light in corresponding ranges of wavelengths, including the visible light spectrum and the NIR spectrum that may be readily detected by the one or more imagers (e.g., the stereoscopic imager 202) of the camera apparatus 44. The operation of the camera apparatus 44 may be controlled by a camera controller 206, which may incorporate processors and/or memory devices configured to perform the various procedures discussed herein.

In addition to the camera apparatus 44, the head-mounted display device 12 may incorporate the display screen 26, which may correspond to a transparent display screen through which the local environment presented in the surgical field 24 may be viewed with the display information 14 and/or augmented or simulated information superimposed thereover. In operation, the head-mounted display device 12 may communicate the image stream 124 to the image processing server 70*a* and receive the augmented reality data or surgical guides 14*b* via a device network 210 or network interface that may implement various wireless and/or wired communication protocols as discussed herein. In this way, the image stream 124 may be captured by the camera apparatus 44 and communicated to the image processing server 70*a* to identify the image features 50 and tracking features 52 to enable the registration process 40 and/or drift correction process 130 as discussed herein.

As shown in FIG. 9, the image processing server 70*a* may incorporate one or more processors 212, including one or more graphic processors (GPUs) that may be implemented for a feature extraction module 212*a* or one or more computational processing units (CPUs) that may provide for pose-calculation and alignment module 212*b*. The pose-calculation and alignment module 212*b* may be implemented to calculate the camera pose 100 relative to the anatomy 22 and/or align or calculate offsets among the various coordinate systems 54 as discussed herein.

In addition to processing the images or frames from the image stream 124, the image processing server 70*a* may be implemented to generate the one or more surgical guides 14*b*, which may be in the form of various images and/or graphics generated by a visualization module 214. In operation, each of the processors 212 and corresponding modules 212*a*, 212*b*, 214 may access local memory devices (not shown) and/or remote memory and/or databases associated with the surgical planning system 200 to access the patient data 42, procedural steps, instructions, surgical guides, patient models (e.g. three-dimensional models from scans), or various surgical or medical information that may be associated with a patient and/or surgical. Accordingly, the image processing server 70 may be implemented in various configurations to support the operation of the visualization system 10.

More generally, various devices and components of the visualization system 10 and the surgical planning system 200 may incorporate a wide variety of specialty or general purpose computational units and corresponding memory devices that may be communicatively accessed to process the various routines and access the corresponding information and/or data required to operate the visualization system 10. For example, the one or more processing units of the system 10 may include one or more graphic processing units, associated processing units, programmable arrays, and/or various computational circuits that may be programmed to facilitate the operations discussed herein. Similarly, the various memory devices accessed by the processing units may correspond to various forms of computer-readable storage media such as random access memory (RAM), flash memory, read-only memory (ROM), programmable ROM (PROM), or similar forms of non-transitory, machine-readable storage media. Accordingly, the various operations of the controllers, processors, and/or servers as discussed herein may be implemented or enabled by utilizing a wide variety of processing units and corresponding memory devices, each of which may be selected based on the particular application associated with the underlying operation.

As previously discussed, the visualization system 10 may also be in communication with a surgical planning system 200, which may incorporate the planning server 70*b*. The planning system 200 may incorporate various planning workstations 220 utilized to generate various surgical plans and process the patient data 42 for each patient 20. For example, the patient data 42 as discussed herein may be stored in a patient record database 222, which may be populated with a variety of patient information including medical history, scanning information, procedural plans, etc. As discussed herein, the patient data 42 may correspond to one or more bone models and corresponding information that may be obtained via various medical scanning devices, such as computerized tomography (CT), magnetic resonant imaging (MRI) machines, and/or X-ray machines. Based on the patient data 42, an operator or computerized routine of each of the planning workstations 220 may generate surgical plans for operations associated with the patient data 42 based on the specific type of procedure, implant, anatomic morphologies, or specific techniques associated with the surgical procedure for implementation with the visualization system 10. Once prepared, a surgical plan may be generated by the surgical planning system 200 and stored in the planning server 70*b* for access by the visualization system 10. Additionally, the surgical planning system 200 may provide for a surgeon or provider access portal 224, which may provide controlled access to one or more surgical plans for a specific patient or a group of patients associated with a surgeon or provider. Via the access portal 224, the surgeon or provider may view, revise, and/or make various updates to the surgical plan preoperatively in preparation for a specific procedure or group of procedures. In this way, the surgical planning system 200 may provide for assisted surgical planning while also supporting customization by the surgeon or medial professional 28 for implementation of the visualization system 10.

Finally, in various implementations, the device network 210 may further be in communication with one or more surgical control consoles 230. The surgical control consoles may correspond to control devices or controllers for various surgical devices including, but not limited to, electric cautery tools, ablation probes, resection tools (e.g., shavers, drills, saws, etc.), surgical pumps (e.g., in-flow/out-flow pumps, etc.), insufflation devices, and/or various imaging or visualization devices (e.g., endoscopes, arthroscopes, laparoscopes, etc.). Accordingly, the visualization system 10 may be flexibly configured to support various steps of surgical procedures, including the operation of various surgical tools or devices that may be in communication with the device network 210 via the one or more surgical consoles 230. Though discussed in reference to specific devices, particularly the head-mounted display 12, it shall be understood that the visualization system 10 may be implemented in a variety of flexible implementations.

The implementations described in the disclosure may be implemented in hardware, software, firmware, middleware, microcode, or any combination thereof. For a hardware implementation, the processing unit may include one or more ASICs (Application Specific Integrated Circuits), DSPs (Digital Signal Processing), DSPDs (DSP Devices), PLDs (Programmable Logic Devices), FPGAs (Field-Pro Grammable Gate Array), general-purpose processor, controller, microcontroller, microprocessor, other electronic unit, or combination thereof for performing the functions described in this disclosure.

For a software implementation, the techniques described in the embodiments of this disclosure can be implemented through modules (e.g., processes, functions, etc.) that perform the functions described in the embodiments of this disclosure. The software codes are stored in memory and executed by the processor. Memory can be implemented within the processor or external to the processor.

The device network as discussed herein could be any local area network (LAN), wireless local area network (WLAN), Intranet, Extranet, or any other appropriate architecture or system that facilitates communications in a network environment. The device network may further include any suitable communication link, such as wireless technologies (e.g., IEEE 802.11, 802.16, Wi-Fi, etc.), cellular technologies (e.g., 3G, 4G, etc.), etc., or any combination thereof. The device network may also include configurations capable of transmission control protocol/Internet protocol (TCP/IP) communications, user datagram protocol/IP (UDP/IP), or any other suitable protocol, where appropriate and based on particular needs.

According to some aspects of the disclosure, a method for tracking patient features in a surgical field, the method comprising: capturing an image stream with a camera, the image stream comprising a plurality of frames in a field of view demonstrating image features representative of the patient features of a patient anatomy; identifying a first feature set comprising a first plurality of the image features in a tracking region of the field of view of the image stream; monitoring a relative motion among the first plurality of the image features in the image stream over time; identifying a plurality of tracking features as a second feature set comprising a second plurality of the image features by filtering at least one moving feature of the first plurality of the image features in response to the relative motion of the at least one moving feature; and tracking a location and orientation of the patient anatomy among feature locations of the plurality of tracking features.

According to various aspects, the disclosure may implement one or more of the following features or configurations in various combinations:

- tracking a pose of the camera relative to the patient anatomy in response to the feature locations;
- generating and/or presenting augmented display data on a display in a predetermined position or orientation relative to the patient anatomy in response to the pose of the camera.
- monitoring the relative motion among the feature locations of the plurality of tracking features for additional moving features;
- filtering the additional moving features from the tracking features identified in the image stream over time;
- generating augmented display data presented on a display in a predetermined position or orientation relative to the patient anatomy;
- the display data is a surgical guide that aligns a surgical tool with the patient anatomy;
- associating a scale of the patient features of the patient anatomy to the image features, wherein the scale is determined based on depth information captured with the image stream or a known proportion of the patient features in patient data;
- at least one of the first feature set and the second feature set are identified based on a combination of two or more of the plurality of frames captured over a period of time;
- the tracking region is defined relative to a point of interest of the patient anatomy for the surgical procedure;
- setting dimensions of the tracking region according to predetermined proportions relative to the point of interest of the surgical procedure;
- adjusting the dimensions of the tracking region in response to the relative motion among the feature locations of the plurality of tracking features;
- the dimension of the tracking region are at least one of increased in response to the relative motion among the feature locations being located outside a boundary of the tracking region; and decreased in response to the relative motion among the feature locations being located inside a boundary of the tracking region;
- the dimensions of the tracking region are decreased along a perimeter of the tracking region in response to the relative motion among the feature locations located along the perimeter;
- identifying one or more of the image features defining a disruptive object, wherein the one or more of the image features is filtered from the image features from which the plurality of tracking features is identified;
- the disruptive object corresponds to an unreliable tracking feature that may unexpectedly change resulting in a tracking error in the location or orientation of the patient anatomy;
- the disruptive object is one of a retractor, a drape, a soft tissue, a surgical tool, or a loose implant;
- the relative motion among first tracking features is determined by comparing the feature locations to corresponding image features identified in a plurality of setup images captured upon registering a pose of the camera to the patient anatomy;

the image features are identified based on two-dimensional representations of three-dimensional features identified from the plurality of setup images;

selecting predefined reference points of the patient features on the patient anatomy; capturing a plurality of setup images of the patient features from a plurality of perspectives; identifying the image features representative of the patient features in the plurality of setup images; and aligning a patient scan data of the patient features based on the location and orientation of the patient anatomy;

the predefined reference points are input intraoperatively;

the predefined reference points are defined in a surgical plan preoperatively;

the predefined reference points are input by aligning an input device with the predefined reference points according to the surgical plan;

displaying the predefined references points on an anatomic model of the patient anatomy demonstrating locations of the reference points from the surgical plan;

the patient anatomy is an exposed portion of bone depicted in the setup images;

the patient scan data is three-dimensional scan data of the patient anatomy from a medical scanning device (e.g., CT scanner, MRI scanner); and/or the patient features correspond to anatomic features of an anatomy of interest proximate to a surgery site.

According to another aspect of the disclosure, a surgical visualization system comprises: at least one camera configured to capture an image stream, the image stream comprising a plurality of frames in a field of view demonstrating image features representative of the patient features of a patient anatomy; a display comprising a screen positioned between a user and the field of view captured by the camera; and at least one controller in communication with that at least one camera and the display, the at least one controller configured to: identify a first feature set comprising a first plurality of the image features in a tracking region of the field of view of the image stream; monitor a relative motion among the first plurality of the image features in the image stream over time; identify a plurality of tracking features as a second feature set comprising a second plurality of the image features by filtering at least one moving feature of the first plurality of the image features in response to the relative motion of the at least one moving feature; track a location and orientation of the patient anatomy among feature locations of the plurality of tracking features; and generate display information presented on the display in a predetermined relationship to the patient anatomy.

According to various aspects, the disclosure may implement one or more of the following features or configurations in various combinations:

the screen is at least partially transparent, presenting the patient features therethrough;

the at least one controller is further configured to: align a patient scan data of the patient features to the patient anatomy based on the location and orientation of the patient anatomy;

the display information is generated on the display in alignment with the patient anatomy relative to a viewing perspective of a viewer of the display.

the display information is a surgical guide configured to align a surgical procedure with the anatomy of the patient;

the controller is further configured to align the surgical guide with the patient anatomy on the display by tracking a pose of the at least one camera relative to the plurality of tracking features; and/or changes of the pose of the camera are tracked over time based on the feature locations of the plurality of tracking features.

According to yet another aspect of the disclosure, a method for tracking patient anatomy in a surgical field, the method comprising: capturing an image stream with a camera, the image stream comprising a plurality of frames in a field of view demonstrating image features representative of the patient anatomy; identifying a first feature set comprising a first plurality of the image features in a tracking region of the field of view of the image stream; identifying one or more of the image features defining a disruptive object, wherein the disruptive object is identified as a predetermined object or class of objects that change in position or form over time; identifying a plurality of tracking features as a second feature set comprising a second plurality of the image features by filtering the image features of the disruptive object from the first plurality of the image features; and tracking a location or orientation of the patient anatomy based on the plurality of tracking features.

It will be understood that any described processes or steps within described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structures and methods without departing from the concepts of the present device, and further it is to be understood that such concepts are intended to be covered by the following claims unless these claims by their language expressly state otherwise.

The above description is considered that of the illustrated embodiments only. Modifications of the device will occur to those skilled in the art and to those who make or use the device. Therefore, it is understood that the embodiments shown in the drawings and described above are merely for illustrative purposes and not intended to limit the scope of the device, which is defined by the following claims as interpreted according to the principles of patent law, including the Doctrine of Equivalents

The invention claimed is:

1. A method for tracking patient features in a surgical field, the method comprising:

capturing an image stream with a camera, the image stream comprising a plurality of frames in a field of view demonstrating image features representative of the patient features of a patient anatomy;

identifying a first feature set comprising a first plurality of the image features in a tracking region of the field of view of the image stream;

monitoring a relative motion among the first plurality of the image features in the image stream over time;

identifying a plurality of tracking features as a second feature set comprising a second plurality of the image features by filtering at least one moving feature of the first plurality of the image features in response to the relative motion of the at least one moving feature; and tracking a location and orientation of the patient anatomy among feature locations of the plurality of tracking features.

2. The method according to claim 1, further comprising: tracking a pose of the camera relative to the patient anatomy in response to the feature locations.

3. The method according to claim 2, further comprising: presenting augmented display data on a display in a predetermined position or orientation relative to the patient anatomy in response to the pose of the camera.

4. The method according to claim 3, wherein the augmented display data is a surgical guide that aligns a surgical tool with the patient anatomy.

5. The method according to claim 1, further comprising: associating a scale of the patient features of the patient anatomy to the image features, wherein the scale is determined based on depth information captured with the image stream or a known proportion of the patient features in patient data.

6. The method according to claim 1, further comprising: monitoring the relative motion among the feature locations of the plurality of tracking features for additional moving features; and filtering the additional moving features from the tracking features identified in the image stream over time.

7. The method according to claim 1, wherein at least one of the first feature set and the second feature set are identified based on a combination of two or more of the plurality of frames captured over a period of time.

8. The method according to claim 1, wherein the tracking region is defined relative to a point of interest of the patient anatomy for the surgical procedure.

9. The method according to claim 8, further comprising: setting dimensions of the tracking region according to predetermined proportions relative to the point of interest of the surgical procedure.

10. The method according to claim 9, further comprising: adjusting the dimensions of the tracking region in response to the relative motion among the feature locations of the plurality of tracking features.

11. The method according to claim 10, wherein the dimension of the tracking region are at least one of:

increased in response to the relative motion among the feature locations being located outside a boundary of the tracking region; and decreased in response to the relative motion among the feature locations being located inside a boundary of the tracking region.

12. The method according to claim 10, wherein the dimensions of the tracking region are decreased along a perimeter of the tracking region in response to the relative motion among the feature locations located along the perimeter.

13. The method according to claim 1, further comprising: identifying one or more of the image features defining a disruptive object, wherein the one or more of the image features is filtered from the image features from which the plurality of tracking features is identified.

14. The method according to claim 13, wherein the disruptive object corresponds to an unreliable tracking feature that may unexpectedly change resulting in a tracking error in the location or orientation of the patient anatomy.

15. The method according to claim 14, wherein the disruptive object is one of a retractor, a drape, a soft tissue, a surgical tool, or a loose implant.

16. The method according to claim 1, wherein the relative motion among first tracking features is determined by comparing the feature locations to corresponding image features identified in a plurality of setup images captured upon registering a pose of the camera to the patient anatomy.

17. A surgical visualization system comprising:

at least one camera configured to capture an image stream, the image stream comprising a plurality of frames in a field of view demonstrating image features representative of the patient features of a patient anatomy;

a display comprising a screen positioned between a user and the field of view captured by the camera; and at least one controller in communication with that at least one camera and the display, the at least one controller configured to:

identify a first feature set comprising a first plurality of the image features in a tracking region of the field of view of the image stream;

monitor a relative motion among the first plurality of the image features in the image stream over time;

identify a plurality of tracking features as a second feature set comprising a second plurality of the image features by filtering at least one moving feature of the first plurality of the image features in response to the relative motion of the at least one moving feature;

track a location and orientation of the patient anatomy among feature locations of the plurality of tracking features; and generate display information presented on the display in a predetermined relationship to the patient anatomy.

18. The system according to claim 17, wherein the screen is at least partially transparent, presenting the patient features therethrough.

19. The system according to claim 17, wherein the at least one controller is further configured to:

align a patient scan data of the patient features to the patient anatomy based on the location and orientation of the patient anatomy.

20. The system according to claim 19, wherein the display information is generated on the display in alignment with the patient anatomy relative to a viewing perspective of a viewer of the display.

21. A method for tracking patient anatomy in a surgical field, the method comprising:

capturing an image stream with a camera, the image stream comprising a plurality of frames in a field of view demonstrating image features representative of the patient anatomy;

identifying a first feature set comprising a first plurality of the image features in a tracking region of the field of view of the image stream;

identifying one or more of the image features defining a disruptive object, wherein the disruptive object is identified as a predetermined object or class of objects that change in position or form relative to the patient anatomy over time;

identifying a plurality of tracking features as a second feature set comprising a second plurality of the image features by filtering the image features of the disruptive object from the first plurality of the image features; and tracking a location or orientation of the patient anatomy based on the plurality of tracking features.

* * * * *